(12) United States Patent
Dirschus et al.

(10) Patent No.: US 9,585,539 B2
(45) Date of Patent: Mar. 7, 2017

(54) METHOD FOR OPERATING AN AUTOMATIC CLEANING MACHINE

(71) Applicants: MEIKO MASCHINENBAU GMBH & CO. KG, Offenburg (DE); Jürgen Dirschus, Schutterwald (DE); Philipp Huber, Oberkirch (DE)

(72) Inventors: Jürgen Dirschus, Schutterwald (DE); Philipp Huber, Oberkirch (DE)

(73) Assignee: MEIKO MASCHINENBAU GMBH & CO. KG, Offenburg (DE)

( * ) Notice: Subject to any disclaimer, the term of this patent is extended or adjusted under 35 U.S.C. 154(b) by 242 days.

(21) Appl. No.: 14/391,918

(22) PCT Filed: May 7, 2013

(86) PCT No.: PCT/EP2013/001359
§ 371 (c)(1),
(2) Date: Oct. 10, 2014

(87) PCT Pub. No.: WO2013/167268
PCT Pub. Date: Nov. 14, 2013

(65) Prior Publication Data
US 2015/0106710 A1  Apr. 16, 2015

(30) Foreign Application Priority Data
May 9, 2012 (DE) ............ 10 2012 009 091.9

(51) Int. Cl.
*G06F 3/0484* (2013.01)
*A47L 15/42* (2006.01)
(Continued)

(52) U.S. Cl.
CPC ....... *A47L 15/4293* (2013.01); *A47L 15/0063* (2013.01); *A61L 2/24* (2013.01);
(Continued)

(58) Field of Classification Search
CPC ............ A47L 15/4293; A47L 15/0063; A47L 2301/08; A47L 2501/26; A47L 2501/36; G06F 3/04847
See application file for complete search history.

(56) References Cited

U.S. PATENT DOCUMENTS 6,903,831 B1   6/2005   Rapke-Kraft et al.
7,951,342 B2   5/2011   Benning et al.
(Continued)

FOREIGN PATENT DOCUMENTS

DE   11 2008 000 499 T5   4/2010
DE   100 52 014 B4   1/2011
(Continued)

OTHER PUBLICATIONS

International Search Report and Written Opinion of the International Searching Authority mailed on Oct. 7, 2013 for PCT Patent Application No. PCT/EP2013/001359, 13 pages.

*Primary Examiner* — Anil Bhargava
(74) *Attorney, Agent, or Firm* — Kilpatrick Townsend & Stockton LLP

(57) ABSTRACT

The invention relates to a method for operating an automatic cleaning device, in particular an industrially usable dishwasher or cleaning and disinfection device with a man-machine interface and a display with buttons. Symbols for the operation and/or an ongoing process are illustrated on the man-machine interface. An interaction of an operator with the man-machine interface is effected via buttons. Depending on the requirements of the operator, context-sensitive help is retrieved via a retrieval, said help accessing a stored information supply comprising image formats, PNG formats, drawings, maintenance lists, spare parts lists and/or databases, which are offered to the operator.

11 Claims, 5 Drawing Sheets

(51) Int. Cl.
  *A61L 2/24* (2006.01)
  *G05B 23/02* (2006.01)
  *G06F 9/44* (2006.01)
  *A47L 15/00* (2006.01)

(52) U.S. Cl.
  CPC ..... *G05B 23/0216* (2013.01); *G06F 3/04847* (2013.01); *G06F 9/4446* (2013.01); *A47L 2301/04* (2013.01); *A47L 2301/08* (2013.01); *A47L 2501/26* (2013.01); *A47L 2501/36* (2013.01); *A61L 2202/17* (2013.01)

(56) References Cited

U.S. PATENT DOCUMENTS

| | | |
|---|---|---|
| 8,332,773 B2 | 12/2012 | Husoy et al. |
| 8,356,257 B2 | 1/2013 | Husoy et al. |
| 8,417,357 B2 | 4/2013 | Husoy et al. |
| 8,479,097 B2 | 7/2013 | Husoy et al. |
| 2001/0025349 A1* | 9/2001 | Sharood ............. G06Q 30/0235 713/340 |
| 2001/0049846 A1* | 12/2001 | Guzzi .................... D06F 33/02 8/158 |
| 2003/0083789 A1* | 5/2003 | Kalley .................... G09B 5/06 701/1 |
| 2003/0143946 A1* | 7/2003 | Grzeczkowski ... H04N 7/17309 455/3.05 |
| 2005/0080879 A1* | 4/2005 | Kim .................... H04L 12/2803 709/219 |
| 2005/0154985 A1 | 7/2005 | Burkhart et al. |
| 2008/0130520 A1* | 6/2008 | Ebrom ...................... G06F 9/54 370/254 |
| 2010/0088627 A1 | 4/2010 | Enkerud et al. |
| 2010/0139720 A1* | 6/2010 | Beaudet .............. A47L 15/4293 134/57 D |
| 2012/0031432 A1 | 2/2012 | Beaudet et al. |
| 2013/0212516 A1 | 8/2013 | Husoy et al. |

FOREIGN PATENT DOCUMENTS

| | | |
|---|---|---|
| DE | 10 2010 022141 A1 | 11/2011 |
| DE | 102010022141 A1 | 11/2011 |
| DE | 10 2011 050951 A1 | 2/2012 |
| EP | 1 965 301 A1 | 9/2008 |

* cited by examiner

METHOD FOR OPERATING AN AUTOMATIC CLEANING MACHINE

PRIORITY CLAIM

This application is a national stage application of PCT/EP2013/001359, filed May 7, 2013, which claims priority to German Patent Application No. 10 2012 009 091.9, filed on May 9, 2012, the entireties of which are incorporated herein by reference.

TECHNICAL FIELD

The present invention relates to a method for operating an automatic cleaning device and an automatic cleaning device. The automatic cleaning device may be either a dishwasher or a cleaning and disinfection device. The dishwasher is, in particular, an industrially usable dishwasher, such as, for example a tunnel dishwasher, whether it be a belt tunnel dishwasher or a rack conveyor dishwasher or a program automat of the type used in industrial washing. The cleaning and disinfection device is one which is designed in particular for handling containers for human excreta.

PRIOR ART

DE 100 52 014 B4 relates to a method for controlling an operating system for a printing machine with a graphical user interface. The method serves to control the printing machine through actions of an operator of the printing machine in context with the user interface and with electronic documentation. The electronic documentation is displayed selectively on the user interface by actions of the operator in context with the user interface. The electronic documentation contains operating instructions for the printing machine, a spare parts catalogue for the printing machine, spare part numbers and spare part drawings, and also maintenance instructions for the printing machine. Furthermore, the electronic documentation comprises a list of allocations between electronic addresses of electronic components in the printing machine and spare part numbers and/or spare part drawings and, if a fault of an electronic component is reported with details of its electronic address, this is indicated on the user interface and allocated spare part numbers and/or spare part drawings are displayed in response to an action of the operator. Furthermore, in the case of a fault, a fault clearance program is called by the operator. Furthermore, a telecommunications connection is set up to a remote service system when the fault clearance program is called or executed.

DE 11 2008 000 499 T5 relates to a method for loading and displaying different process displays on a user interface of an industrial control system. The industrial control system comprises a computer and a display device, and also a computer-implemented workstation application. Furthermore, the control system comprises a multiplicity of process control interfaces which contain one or more software objects for controlling and/or monitoring an object controlled by the control system and which are displayed on the display device. A quantity of the process control interfaces is displayed in the user interface, wherein the process control interfaces are generated by an instance of the workstation application in a designated view. The designated view comprises a corresponding quantity of graphical user interface objects. Each graphical user interface object identifies the corresponding process control interface, which is displayed by means of selection of a first or second graphical user interface object. A changeover is thereby effected between a display of a first process control interface and a display of a second process control interface in the same instance of the workstation application.

Automatic cleaning devices which are used industrially must allow not only specific cleaning and hygiene methods, but also the simplest possible and yet reliable user guidance. Work has been carried out for a long time on optimum concepts for this purpose. The advent of microprocessor controls with correspondingly elaborately designed user interfaces or man-machine interfaces offers the possibility of increasing convenience for the users and at the same time handling reliability and operational reliability. The user interfaces are intended to enable the simplest possible interaction for the user by means of suitable help. The man-machine interface is accordingly intended to have a suitable context sensitivity which provides, on the one hand, an optimum reference to the action just carried out and, on the other hand, also information which directly matches the instantaneous operating condition.

Currently used known help systems in many cases offer inadequate context sensitivity. For example, currently used help systems display no additional information or they refer to documents, for example operating instructions, which are not located in the immediate vicinity of operating personnel or to which the operator has no direct access. A still very widespread procedure entails the provision of operating personnel with a quick start guide, e.g. a page in a waterproof design. The essential steps for the operation, daily cleaning and maintenance of the automatic cleaning device are shown in this quick reference guide. Furthermore, instructions for loading the automatic cleaning device can be given in the quick reference guide. A substantial disadvantage of this form of instruction lies in the risk that the instruction will be lost or will become so damaged that it is no longer available to operating personnel. A missing instruction causes errors in the operation, disruptions to the operating process or inadequate cleaning results. In the event of doubt, service personnel also do not have the entire required documentation of the machine in the form of manuals and the like, or a current version thereof, directly available in situ. This unsatisfactory situation is to be remedied.

DISCLOSURE OF THE INVENTION

The object of the present invention is to provide an operating system and/or a help system for the operation of an industrial dishwasher or cleaning and disinfection device which has a high degree of context sensitivity and therefore enables a simplified, more reliable operation on the one hand and, on the other hand, a higher useful value for the operator and service personnel in the respective required activities with the operating system or the industrially usable dishwasher or a cleaning and disinfection device.

An operating method is proposed which offers the user additional help which is designed, in particular, as context-sensitive help, so that more detailed information or help is offered to the user for any given items in a menu structure. The handling of the automatic cleaning device is thereby further simplified for the user and an overview of different operating situations possibly to be expected is displayed. In the present connection, context sensitivity is to be understood as the behaviour of an application program which uses information on the context, i.e. the environment of the application program itself in order to adapt its behaviour, i.e.

the behaviour of the application program with regard to this context, i.e. the circumstances prevailing in the immediate vicinity.

The context sensitive help (CSH) proposed according to the invention conveys information on user interfaces of applications in relation to the task carried out by the user (washing personnel, operators, service personnel). The CSH conveys, for example, information on fields and control elements in dialogue fields, descriptions of windows or screen elements, explains message texts and/or provides operating instructions. By means of the concept proposed according to the invention for the operation of an automatic cleaning device, the user is offered the help that is suitable for the current process in a process-dependent manner. The help offering can be used or declined or ignored by the user. The context-sensitive help topics are set out in the respective context-sensitive help by means of allocation IDs and allocation files. If the user accesses context-sensitive help, the allocation ID and the name of the help file, i.e. the corresponding allocation file, are sent to an integrated file management software/file management system. This system matches the allocation ID to a topic ID and an HTM file name, so that the correct topic can be displayed to the user.

In the operation of known interfaces, tool tips are displayed whenever e.g. the mouse is placed on a control element which is displayed on the user interface. Normally, the display of a tooltip is automatically closed again after a certain time span. It may arise here that the text of the tool tip is too long to be able to be read by the user or the display time is selected as too long, so that the appearance of the tooltip already represents a disruption for the users.

In the context-sensitive help (CSH) proposed according to the invention, the user can himself decide when and for how long he wants to see the corresponding display of the tooltip. The display is parameterisable, for example the display period can be linked to the actuation period of a corresponding key.

By means of the context-sensitive help (CSH), e.g. by means of the display of images, for example in PNG data format, for different message and fault displays, the information can be made available in a language-independent form to all users. For specific messages or status displays which are provided in the process, for example in relation to temperatures, the corresponding situations can be indicated and explained more precisely by means of stored diagrams. The context-sensitive help (CSH), which is available at all times, transparently presents the comprehensive menu structure to the user with the aid of a variety of multimedia information carriers. The operating levels and functions offered are always explained in detail with the stored information via the extended help system. This offers an extended technical support in which an interaction is carried out between the user and the control in relation to the respective event or the respective function.

The context-sensitive help which is integrated into the machine control comprises digital media, such as text or graphics; in an extension stage, the presentation of images, for example a video film, an audio playback, e.g. a voice announcement, or a dictated instruction for fault location may also be included.

The multimedia libraries are provided, on the one hand, on the man-machine interface directly on the machine and, on the other hand, also by means of a wireless data transfer, for example via a Bluetooth interface for a mobile device or an external computer system, for example a PDA (Personal Digital Assistant).

Via the variously configured interfaces for the control system of the industrially usable automatic cleaning device, new findings or new solutions to problems can also be stored in the control, for example in a library. An occurring current situation can thus be documented in the form of images, videos, etc. and can be retrieved for immediate remedial action for recurring problem cases. A learning behaviour of the context-sensitive help thereby occurs which can be profitably used over the entire lifecycle of the machine. Context-sensitive help (CSH) can be extended and continuously expanded on a machine-related basis. A maximum benefit compared with previously used conventional help systems is available to the user through application of the operating concept proposed according to invention.

The user interface of a control system of an industrial dishwasher or a cleaning and disinfection device is designed, for example, so that it provides operating levels with different functional scope and concomitant display scope. The access authorization for the different levels can be regulated, for example, by a required authentication of the user, e.g. via the required input of a password or code or PIN; other methods are similarly conceivable.

The top level is, for example, the level at which the machine is operated by washing personnel. It appears as soon as the machine is switched on. A further, second level is, for example, a level protected by code input, at which specially trained personnel of the operator of the dishwasher have access. Here, for example, the kitchen manager can retrieve the operating data. A further, third level is, for example, a level similarly protected by code input, to which only service personnel of the machine manufacturer have the code or obtain access. Here, for example, machine parameters can be modified, operating faults can be analysed or repairs can be carried out. These levels can also be referred to as authorization levels.

For each menu item of the operating menu, help texts are stored as images, for example in the form of PNGs, and are offered to the user. Other data formats are similarly applicable. The navigation between the individual menu items is defined via a formal language and therefore allows flexibility. The "context" i.e. the current operating status of the automatic cleaning device or the currently set authorization level, differentiates the corresponding available files, e.g. in the form of PNGs, and therefore simultaneously the useful content of help screen representations. The help screens may, for example, be schematic representations or may be designed in the form of real illustrations, where appropriate with extension.

For example, on a cleaning and disinfection device with the status "ready for operation" and with the washing chamber door open, an image can be displayed on which it is evident how the vessels to be cleaned are correctly inserted into the holder provided for that purpose. Valuable instructions are thereby given to the user, so that an optimum cleaning and disinfection result is achieved.

On an industrial dishwasher, after washing personnel have selected the self-cleaning option, a video film, for example, can be made available, in which it is shown which and how the last manual actions are to be carried out at the end of the operation, e.g. that the tank filter must be removed from the washing chamber and must be manually emptied at the end of the operation.

It is possible for the user, according to his authorization, to store information independently, by means of a wireless data transfer, e.g. via the Bluetooth interface, directly in the machine control, for example on an integrated memory card. Thus, for example, PNGs can be stored under the user's personal responsibility and according to the individual requirement. For example, method instructions which the operator has drawn up can be simply implemented in the system with no action required on the part of the manufacturer of the device, i.e. the industrially usable automatic cleaning device.

In addition, the system offers a document server implemented in the machine control, e.g. on a processor unit, which can be used to store operating instructions, service instructions, spare parts lists or a circuit diagram that currently goes with the respective machine.

An optional facility also exists to provide Internet access to keep the aforementioned documents up-to-date via a defined interface, so that the respective latest version of said documents is always available to the user.

Specifically in the case of fault messages, the context reference can be implemented according to a top-down principle. Here, the respective context sensitivity is used to provide the user, according to his authorization allocation, with instructions for fault location via suitable details, e.g. in the form of PNG files. The help may, for example, provide instructions indicating which screws or covers on the automatic cleaning device are to be removed in order, for example, to reach a defective sensor or actuator. Associated safety instructions can additionally be shown.

In the context-specific detail image of the information/fault display, corresponding limit values and a history of the last activities allocated to the sensor or actuator can be output on the machine. Information that is specifically important for the service can thus be derived directly from the displayed help window. Corresponding detail images are not displayed until the corresponding event has occurred or is imminent on the automatic cleaning device. For example, the location and position of the cleaning agent or rinse aid supply container, for example in the case of an empty message, can be displayed accordingly in precise detail.

BRIEF DESCRIPTION OF THE DRAWING

The invention is described in more detail below with reference to the drawing, wherein.

DESIGN VARIANTS

Figure 1:
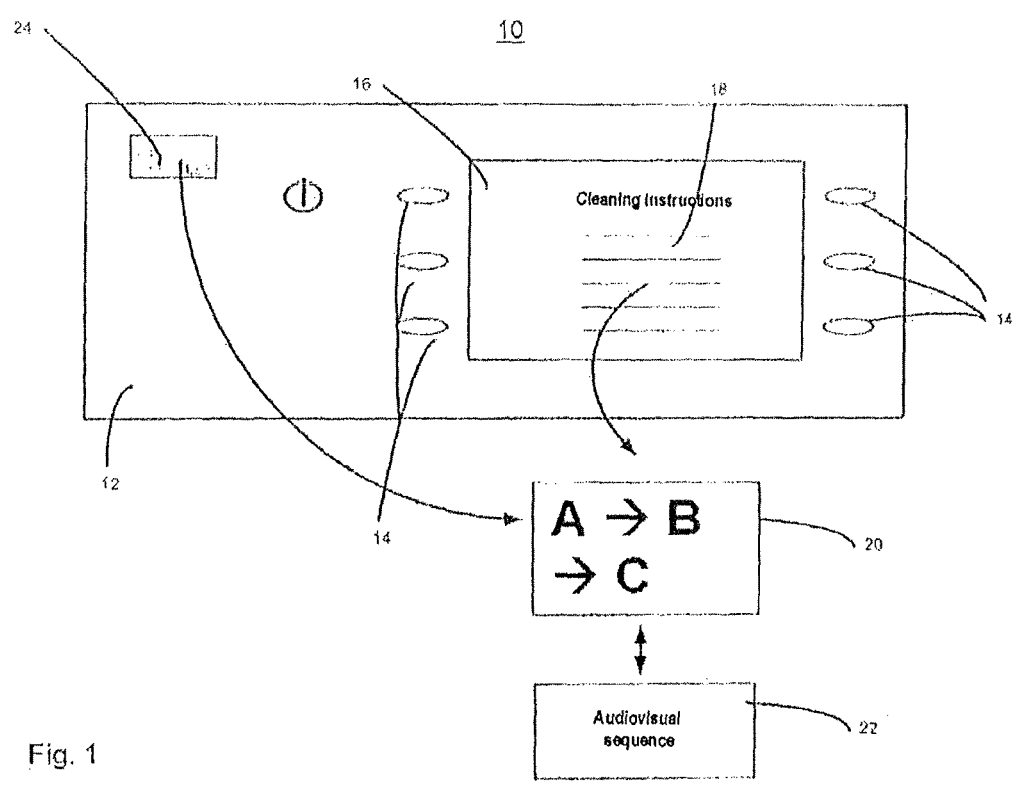
FIG. 1 shows the representation of a man-machine interface with touch-sensitive buttons.

The representation according to FIG. 1 shows the view of a man-machine interface via which an automatic cleaning device, for example a rack conveyor dishwasher, a belt tunnel dishwasher, an industrially usable program automat or a cleaning and disinfection device is controlled. The representations according to FIGS. 1 to 3 relate to the operation of a cleaning device of this type by the user, for example by washing personnel, while the representations according to FIGS. 4 and 5 relate to a service level 40, which is normally retrieved by qualified service personnel of the machine manufacturer and is not accessible to washing personnel.

The user interface of a control system of an industrial dishwasher or cleaning and disinfection device is frequently structured so that operating levels exist with different functional scope and concomitant display scope. The access authorization for the different levels is regulated by a different authentication, for example by the required input of a password or code or a PIN.

The top, first, level is, for example, the level at which the machine is operated by washing personnel. It appears as soon as the machine is switched on. A further, second level is, for example, a level protected by code input, at which specially trained personnel of the operator of the dishwasher have access. Here, for example, the kitchen manager can retrieve the operating data. A further, third level is, for example, a level similarly protected by code input, to which only service personnel of the machine manufacturer have the code or obtain access. Machine parameters, for example, can be modified here.

The aforementioned first, second and third levels, which define operating levels which differ from one another, can be structured in relation to the respective level in such a way that different information requirements can be met, then resulting in different content for the respective individually required help.

At the operator level 10 shown in FIG. 1, the automatic cleaning device is controlled via the operator. For this purpose, the man-machine interface 12 shown in FIG. 1 has buttons 14 which may be designed as touch-sensitive buttons. The man-machine interface 12 comprises a display on which symbols 16 are located, and also a display panel to display the respectively running process or to output messages. The man-machine interface 12 according to the representation in FIG. 1 additionally has a retrieval button 24 via which a context-sensitive help (CSH) 34 described in more detail below can be retrieved. The retrieval button 24 is pressed by the operator according to requirements.

The representation according to FIG. 1 indicates that, for example, the "cleaning instructions" message can be retrieved on the display of the man-machine interface 12. If the operator then presses the retrieval button 24, an overview 20 of the individual steps to be carried out by the operator appears for the "cleaning instructions" menu item. The overview 20 can additionally be output via a variety of multimedia information carriers, for example via a PDA, and a mobile telephone would also be conceivable. The output of the overview 20 shown in FIG. 1 can be extended, for example, via the provision of a video film or an audiovisual sequence. Memories, e.g. SD cards, e.g. integrated into the control, can be considered as multimedia information carriers. The video film provided would be output either on the display of the automatic cleaning device or on the PDA.

Figure 2:
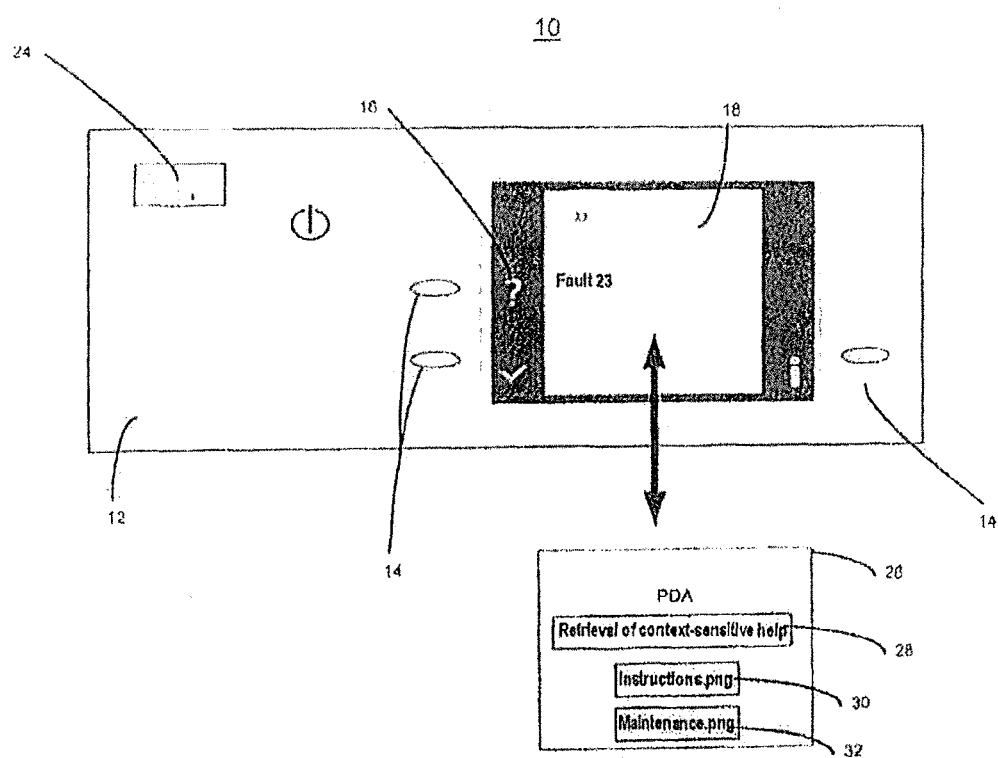
FIG. 2 shows the interaction between a man-machine interface when a fault has occurred and with an external device such as, for example, a Personal Digital Assistant (PDA)

The representation according to FIG. 2 shows the interaction between the man-machine interface and a PDA.

FIG. 2 shows that a fault message is indicated on the display of the man-machine interface 12. A representation of the man-machine interface 12, at the operator level 10, can similarly be found in FIG. 2, analogous to FIG. 1. The man-machine interface 12 or its display has a button 14, which may, for example, be a touch-sensitive button. The symbols 16 are located on the display according to FIG. 2, analogous to the representation according to FIG. 1; furthermore, the man-machine interface 12 according to the representation in FIG. 2 comprises a display on which fault messages can be indicated or a process representation is present. Furthermore, the retrieval button 24, via which assistance or help programs or functions can be retrieved, is located on the man-machine interface.

According to the representation in FIG. 2, the man-machine interface 12 or the control of the automatic cleaning device interacts with a PDA (Personal Digital Assistant) 26. Instead of a PDA 26, an interaction could also take place between a mobile telephone and the man-machine interface, for example via a smartphone or the like. To name one example, a retrieval function 28 which can output a plurality of messages or work instructions or guidance or the like is stored on the PDA 26. In a first with reference number 30 designates a first PNG, for example instructions, while reference number 32 indicates a second PNG, for example maintenance instructions. In the example, a fault is present in the automatic cleaning device control. The man-machine interface 12 or the control now offers context-sensitive help specifically for the indicated fault. If the display on the control is small and if the help could only be processed by the user with some difficulty, the complete content of the context-sensitive help could be transferred to a mobile device with a larger display. A further advantage of the described interaction between the controller and the PDA is that, in the case of large automatic cleaning devices, such as e.g. belt tunnel dishwashers, the PDA with the displayed fault clearance help can also be taken along to the fault location, e.g. at the inlet of the dishwasher. As a result, the distance from the man-machine interface 12 on which the help will be primarily displayed to the fault location no longer represents a hindrance to the user.

In the example shown in FIG. 2, the context-sensitive help is located in the offering of the man-machine interface 12. Said context-sensitive help 34 can be retrieved via the retrieval function 28 stored in the PDA 26, but this does not represent automatism, but rather a decision made by the operator at his own discretion.

Figure 3:
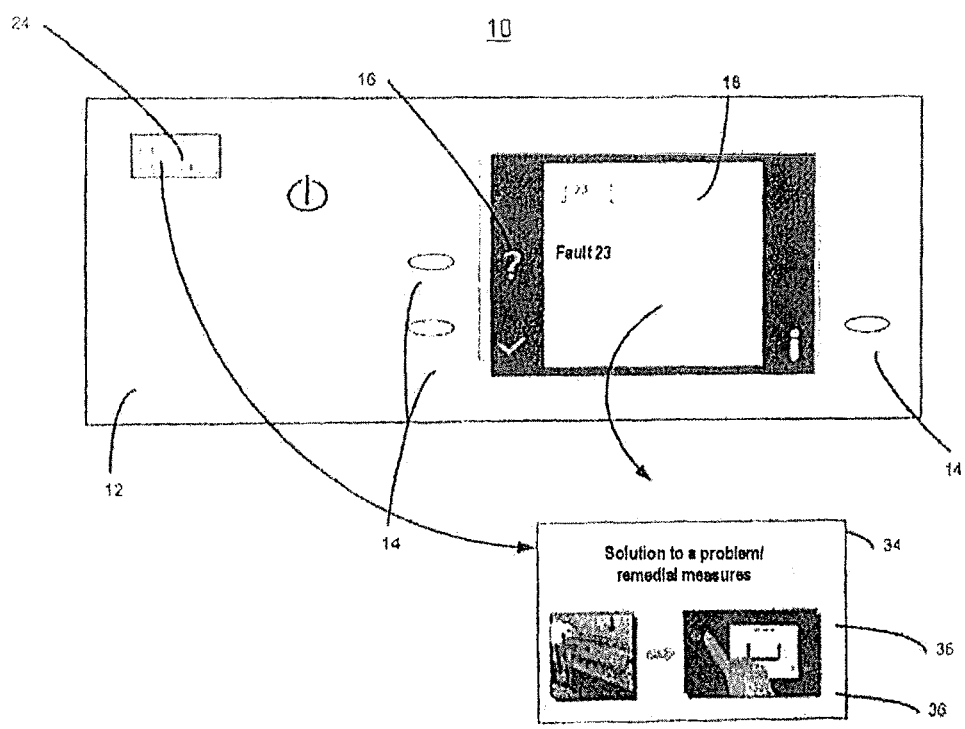
FIG. 3 shows the representation of context-sensitive help which is retrieved by the operator when a fault occurs which is indicated on the display of the man-machine interface.

The representation according to FIG. 3 similarly shows a man-machine interface via which context-sensitive help can be used.

In the representation according to FIG. 3 also, the man-machine interface 12 is operated within the operator level 10 and offers to the operator, on pressing the retrieval button 24, the context-sensitive help 34 which, for example, is then indicated on the display of the man-machine interface 12. The context-sensitive help 34 provides instructions for a solution to a problem or remedial measures 36 which are to be initiated by the operator in order to clear the fault shown on the display of the man-machine interface 12, so that the program can be continued. If, as shown in FIG. 3, the retrieval button 24 on the man-machine interface 12 is pressed, the display changes and options for problem clearance and remedial measures which the operator would have to carry out individually are displayed instead of the fault message. This offering is oriented towards the operating status of the automatic cleaning device, for example an industrial dishwasher, which is known to the man-machine interface 12 through sensors and/or a machine control, so that, within the framework of the context-sensitive help 34, only permissible solutions to a problem or remedial measures are indicated which the operator can carry out at the operating level 10 on his own without having to notify a service technician.

In the representation according to FIG. 3, the content of the display of the man-machine interface is changed by pressing the retrieval button 24 and the fault message is then replaced with the representation of a solution to a problem or remedial measures 36 with which the fault can be cleared.

In this case, the remedial measures or the solution to a problem 36 are stored in the man-machine interface or in the control of the automatic cleaning device and are allocated to the latter according to the fault which has occurred and are retrieved via the retrieval button 24 of the man-machine interface. The user can then determine how long the context-sensitive help 34 remains displayed without the user being patronized by the man-machine interface 12. The user can thereby autonomously decide which information he would like to consider and for what time span.

For each menu item or for each warning or fault message which appears on the display of the man-machine interface 12 according to FIGS. 1 to 3, corresponding help texts can be stored in the form of PNGs or other file formats. The navigation within the help texts is defined via a formal language and can be configured in any given manner. The context and therefore, inter alia, the authorization level also differentiate the corresponding PNGs, cf. items 30, 32 on the PDA 26 according to FIG. 2. As a result, the useful content of the help screen representations can simultaneously be differentiated. Help screens are designed either schematically or in the form of real images with an extension. It is possible for the user, according to his authorization, to store information, e.g. via the Bluetooth interface or with other transmission means, in a memory of the machine control, e.g. on a memory card.

The PNGs 30 and 32 can be stored under the user's own responsibility and according to the individual requirement. For example, method instructions which the operator has drawn up can be simply implemented in the system without the need for any action on the part of the manufacturer of the device, i.e. the industrially usable automatic cleaning device. In addition, the system offers a document server implemented in the machine control, e.g. on a processor unit, which can be used to store operating instructions, service instructions, spare parts lists or a circuit diagram that currently goes with the respective machine. Via an optional Internet access which can also be provided in the man-machine interface 12, or via a defined interface, these documents which are stored in the document server can always be kept up-to-date and the latest version thereof can be retrieved.

The context sensitivity is used to guide the user according to his authorization or level allocation, whether it be at the operating level 10 or at a service level 40 still to be described, via suitable PNGs 30 and 32, to the presumed cause of the fault, for example a defective sensor or a defective actuator. Instructions are given here indicating which screws or covers on the automatic cleaning device are to be removed in order to reach the source of the fault. In addition, corresponding, targeted safety instructions can be output. The authorization level selected, for example, by means of code input, offers protection against unauthorized access and simultaneously excludes a risk to untrained persons.

Limit values, for example, and a history of the last activities on the automatic cleaning device which were allocated to the sensor or actuator are indicated in the context-specific detail image of the fault display, whereby specific service information can be obtained directly from the help window.

The corresponding detail images are not displayed until the corresponding event has occurred on the machine. Thus, for example, the location and position of the cleaning agent or rinse aid supply container—to name one example—can only be displayed in the case of an empty message.

Figure 4:
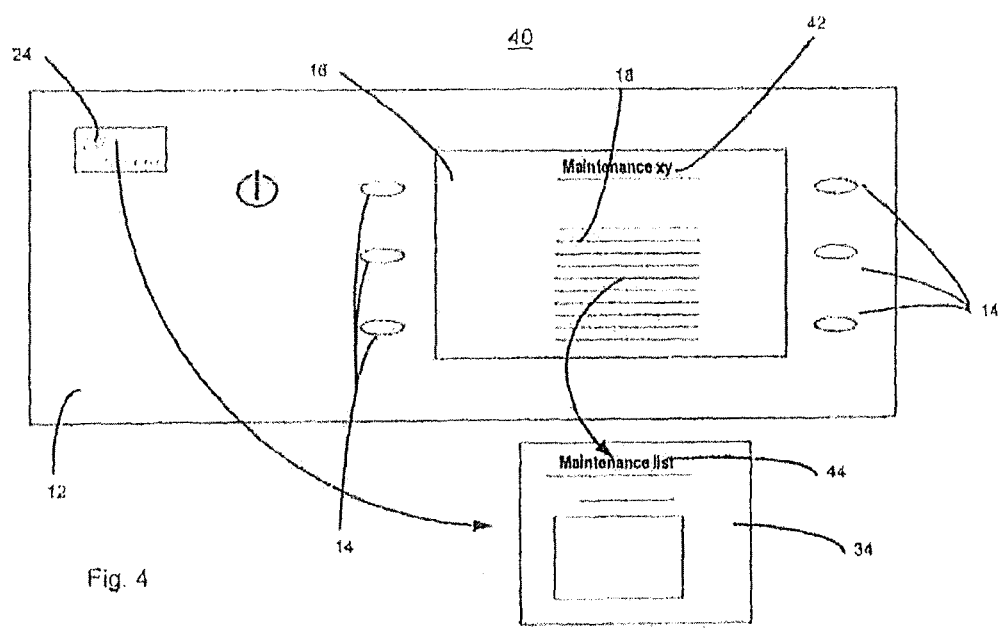
FIG. 4 shows, at a service level of the man-machine interface, the display of a maintenance list or maintenance instruction retrieved by the user.
Figure 5:
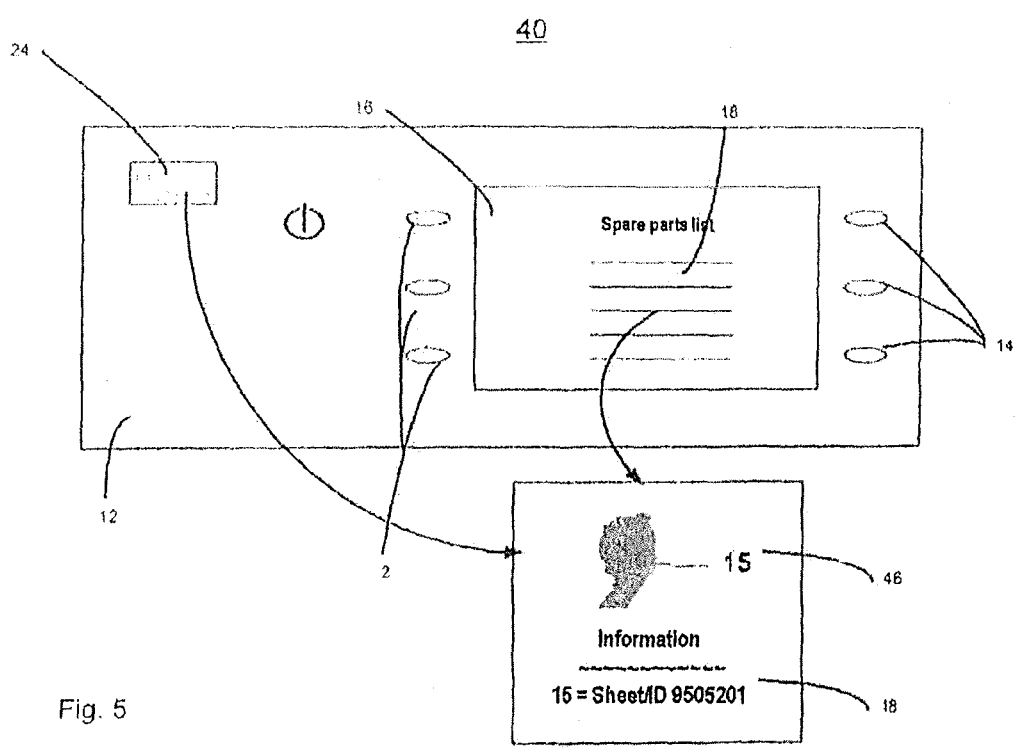
FIG. 5 shows the schematic representation of the retrieval of a spare parts list at the service level of the man-machine interface when retrieved by a service technician.

The man-machine interface 12 is shown at a service level in the representations according to FIGS. 4 and 5.

According to the representations in FIGS. 4 and 5, the man-machine interface 12 is operated by a service technician at the service level 40. In this case, a maintenance message 42 appears on the man-machine interface 12, i.e. on the display allocated to the latter. The maintenance message 42 is, for example, accompanied by a maintenance list or maintenance instruction 44. The latter is known to the man-machine interface 12 and can be retrieved on this by pressing the retrieval button 16. The maintenance list 44 can indicate the work to be undertaken and maintenance intervals which are to be adhered to in order to guarantee a correct functioning of the automatic cleaning device can furthermore be specified on the maintenance list.

For use at the operator level 10 and also for use within the service level 40, information is stored as an information pool on the man-machine interface 12 or in an allocated processor unit for the interaction via the context-sensitive help 34, for example documentation, drawings, spare parts lists, maintenance lists via PNG formats, or collated measurement values from completed cleaning processes in databases. Other suitable data formats can similarly be used. Depending on the current information or help requirement of the operator or of a service technician, the corresponding context-sensitive help 34 can be retrieved via the man-machine interface 12. Thus, brief guidance and maintenance instructions or maintenance lists 44 can thus also be displayed to the operator in the case of maintenance messages also.

FIG. 5 shows how, via the retrieval 24 for the corresponding message 18, for example a spare parts list, a spare parts list 46 appears containing spare part identifications 48. These spare part identifications may, on the one hand, be part numbers and designations, and the spare parts list 46 may furthermore include drawings of the parts, which no longer represents a problem with currently available memory sizes. In the present connection, the man-machine interface, in a manner of speaking, sets up the communication between the operator or service personnel and the control of the automatic cleaning device. For this purpose, the control comprises the man-machine interface 12 via which recourse to parameters stored in memories controls the individual operating conditions of the automatic cleaning device and, if necessary, can also be influenced in a targeted manner. Along with the aforementioned memories, the man-machine interface or user interface, the control also comprises a central processor unit in which all signals are processed and output signals are generated in an output unit according to defined rules. The signals generated in the output unit are forwarded by means of associated control lines to actuators which also form part of the control. The actuators of the automatic cleaning device include e.g. magnetic valves, motors and heaters. The control furthermore normally contains sensors also, such as e.g. temperature sensors, pressure sensors, optical sensors and electromagnetic switching elements.

REFERENCE NUMBER LIST

10 Operator level
12 Man-machine interface
14 Button
16 Symbols
18 Message, process representation
20 Overview/instruction
22 Film, video, audiovisual sequence
24 Retrieval button for context-sensitive help (CSH)
26 Personal Digital Assistant (PDA), mobile device, external computer system
28 Retrieval function
30 First image, first PNG (instruction)
32 Second image, second PNG (maintenance)
34 Context-sensitive help
36 Third image, third PNG (solution to a problem, remedial measure)
40 Service level
42 Maintenance message
44 Maintenance list/Maintenance instruction
46 Spare parts list
48 Spare part identification

The invention claimed is:

1. A method for operating an automatic cleaning device, in particular an industrially usable dishwasher or a cleaning and disinfection device with a man-machine interface and a display with buttons, with the following method steps:
   a) symbols for operation and an ongoing process are displayed on the man-machine interface,
   b) an interaction of an operator with the man-machine interface is effected via buttons, and
   c) depending on the requirement of the operator, context-sensitive help is retrieved and is displayed, said contact-sensitive help accessing a stored information supply comprising at least one of images, drawings, spare parts lists, maintenance lists, audiovisual files, and databases, which are offered to the operator or to a service technician,
   d) multimedia libraries are made available to the automatic cleaning device via the man-machine interface and a wireless data connection for a mobile device,
   e) findings or solutions to problems are stored via the man-machine interface of the automatic cleaning device within a library which is integrated into a control system of the automatic cleaning device,
   wherein at least one of a status and a fault display indicates limit values and a history of last activities allocated to a sensor/actuator, which are derivable directly from a help window as service information.

2. The method according to claim 1, characterized in that the man-machine interface is operated on at least an operator level and at least a further service level.

3. The method according to claim 1, characterized in that information stored for messages or status information is displayed in image file formats.

4. The method according to claim 1, characterized in that information stored for messages of status information is made available in the form of audiovisual data.

5. The method according to claim 1, characterized in that offered operating levels and their functions and intervention options are explained via the context-sensitive help with the information displayed in the man-machine interface.

6. The method according to claim 1, characterized in that a current situation can be documented in the form of images, videos or audiovisual sequences and can be stored in a machine control.

7. The method according claim 1, characterized in that stored situations can be retrieved once more by means of the man-machine interface.

8. The method according to claim 1, characterized in that the context-sensitive help conveys information on fields and control elements in dialogue fields, description of windows or screen elements or message texts.

9. The method according to claim 1, characterized in that information can be stored via wireless data connection internally within the control system, depending on the authorization of the user.

10. The method according to claim 1, characterized in that control of the cleaning device comprises a document server on which at least one of operating instructions, service instructions, spare parts lists, circuit diagrams are stored.

11. The method according to claim 1, characterized in that the context-sensitive help guides a user, taking account of authorization level allocation, via at least one of images and audiovisual content to a presumed fault.

\* \* \* \* \*